(12) United States Patent
Park et al.

(10) Patent No.: US 8,424,385 B2
(45) Date of Patent: Apr. 23, 2013

(54) INSPECTING DEVICE INCLUDING DETACHABLE PROBE

(75) Inventors: Minsu Park, Yongin-Si (KR); Jangmyong Woo, Yongin-Si (KR); Gyungsub Kim, Suwon-Si (KR); Sanghoon Choi, Yongin-Si (KP)

(73) Assignee: Korea Plant Service & Engineering Co., Ltd, Gyeonggi-do (KR)

( * ) Notice: Subject to any disclaimer, the term of this patent is extended or adjusted under 35 U.S.C. 154(b) by 619 days.

(21) Appl. No.: 12/575,650

(22) Filed: Oct. 8, 2009

(65) Prior Publication Data

US 2011/0030478 A1 Feb. 10, 2011

(30) Foreign Application Priority Data

Aug. 6, 2009 (KR) .......................... 10-2009-0072254

(51) Int. Cl.
*G01N 29/24* (2006.01)
*G01N 29/265* (2006.01)

(52) U.S. Cl.
USPC .............................. 73/623; 376/248; 376/249

(58) Field of Classification Search ............ 73/622, 73/623, 625, 626, 628, 634, 637, 641, 601; 376/248, 249
See application file for complete search history.

(56) References Cited

U.S. PATENT DOCUMENTS

| 3,987,666 | A | * | 10/1976 | Blanc et al. | 73/633 |
| 4,131,018 | A | * | 12/1978 | Muller et al. | 73/866.5 |
| 4,569,230 | A | * | 2/1986 | Asty et al. | 73/623 |
| 5,090,259 | A | * | 2/1992 | Shishido et al. | 73/866.5 |

FOREIGN PATENT DOCUMENTS

| JP | 06-016129 | | 1/1994 |
| JP | 09-229868 | | 9/1997 |
| JP | 11-014784 | | 1/1999 |
| JP | 3103990 | | 8/2004 |
| JP | 2004-264199 | | 9/2004 |
| WO | WO 94/02843 | * | 2/1994 |

* cited by examiner

*Primary Examiner* — Peter Macchiarolo
*Assistant Examiner* — Rose M Miller
(74) *Attorney, Agent, or Firm* — Ohlandt, Greeley, Ruggiero & Perle, LLP (57) ABSTRACT

An inspecting device including a detachable probe has a link structure, and thus a subject having various diameters is tested. In addition, since various probes are changeably used in a scanner housing, ultrasonic wave testing and eddy current testing are simultaneously performed.

9 Claims, 6 Drawing Sheets

INSPECTING DEVICE INCLUDING DETACHABLE PROBE

CROSS-REFERENCE TO RELATED PATENT APPLICATION

This application claims the benefit of Korean Patent Application No. 10-2009-0072254, filed on Aug. 6, 2009, in the Korean Intellectual Property Office, the disclosure of which is incorporated herein in its entirety by reference.

BACKGROUND OF THE INVENTION

1. Field of the Invention

The present invention relates to an inspecting device for inspecting a subject having various diameters, and more particularly, to an inspecting device including a detachable probe, which includes a link structure so as to be compatible with various diameters of a subject and performs various tests.

2. Description of the Related Art

A nondestructive inspection method of inspecting internal and external defects of a subject may include a radiograph test and ultrasonic flaw detection. The ultrasonic flaw detection may easily inspect a subject having a great thickness, may immediately detect discontinuous locations and sizes of a subject, does not adversely affect the human body, unlike the radiograph test, and may excellently detect plane defects such as crack.

In particular, in order to inspect defects of a stud bolt used in a unclear reactor by using ultrasonic waves, a hollow probe (or, a transducer) having a cylindrical shape is inserted into a hole formed in the center of the stud bolt, and the hollow probe coupled to a support pole inspects the stud bolt while moving inside the hole. However, in the case of a cylindrical subject (e.g., a unclear reactor stud hole, a turbine hollow axis, various pipes and a tube) having a circular space with a variable dimension, it is required to manufacture the probe according to the dimension of the circular space of the cylindrical subject.

In order to inspect to a subject by using phase array testing, a probe needs to inspect the subject while being closely attached to the subject. However, in the case of a cylindrical subject having a circular space with a variable dimension, it is difficult to closely attach the probe to the circular subject at a pressure appropriate for the circular space of the circular subject, and thus accurate testing may not be performed.

Thus, the inventors of the present disclosure provides an inspecting device that may simultaneously perform visual testing and nondestructive inspection and may be closely attached to a circular space of a subject so as to inspect the subject.

SUMMARY OF THE INVENTION

The present invention provides an inspecting device that may inspect a correct state of a subject by using various probes.

In detail, the present invention provides an inspecting device including a detachable probe, which includes a link structure so as to be compatible with various diameters of a subject and performs various tests.

According to an aspect of the present invention, there is provided an inspecting device for inspecting a cylindrical subject and including a detachable probe, the inspecting device including a frame having a column shape and extending in a longitudinal direction of the column, wherein a guide hole is formed in at least one side of the frame; a head unit including a camera module installed at a fore-end of the frame; a first body unit coupled to the head unit and including a plurality of brackets formed on an external surface of the first body unit; an illumination module unitinstalled into a hole formed in a plate, wherein the plate is placed at the rear of the first body unit; a second body unit surrounds the frame and including a plurality of brackets formed on an external surface of the second body unit; a coiled spring inserted into the first body unit and the second body unit; and a link unit coupled to the plurality of brackets formed on the external surface of the first body unit and the plurality of brackets formed on the external surface of the second body unit so as to be compatible with to tube diameters of the cylindrical subject.

The camera module of the head unit may include a camera and a lens that are inserted into the first body unit; and a circular cap for protecting the camera and the lens.

The camera may include a charge-coupled device (CCD) camera.

A guide pine may be formed on the external surface of the second body unit.

The illumination module unit may include a housing; a light emitting diode (LED) light source inserted into the housing; and a cover unit for protecting the LED light source.

The link unit may include a pair of levers hinged to the plurality of brackets formed on the external surface of the first body unit and the plurality of brackets formed on the external surface of the second body unit; a scanner housing hinged to the pair of levers; rollers formed on both ends of the scanner housing; a scanner formed on an upper end of the scanner housing; and a plate spring formed under the scanner.

The scanner may include a detachable probe. The inspecting device may further include a fixation unit disposed in the scanner housing so that the scanner can be detachable.

Each of the rollers may have a crown shape so as to contact a wall of the cylindrical subject in the form of a line.

The scanner may have the form of an array in which a plurality of ultrasonic wave units are stacked in a width direction. The scanner may include an ultrasonic wave unit or an eddy current inspecting unit, and may include various types of sensors.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in detail by explaining exemplary embodiments of thereof with reference to the attached drawings. Like reference numerals in the drawings denote like elements.

Figure 1:
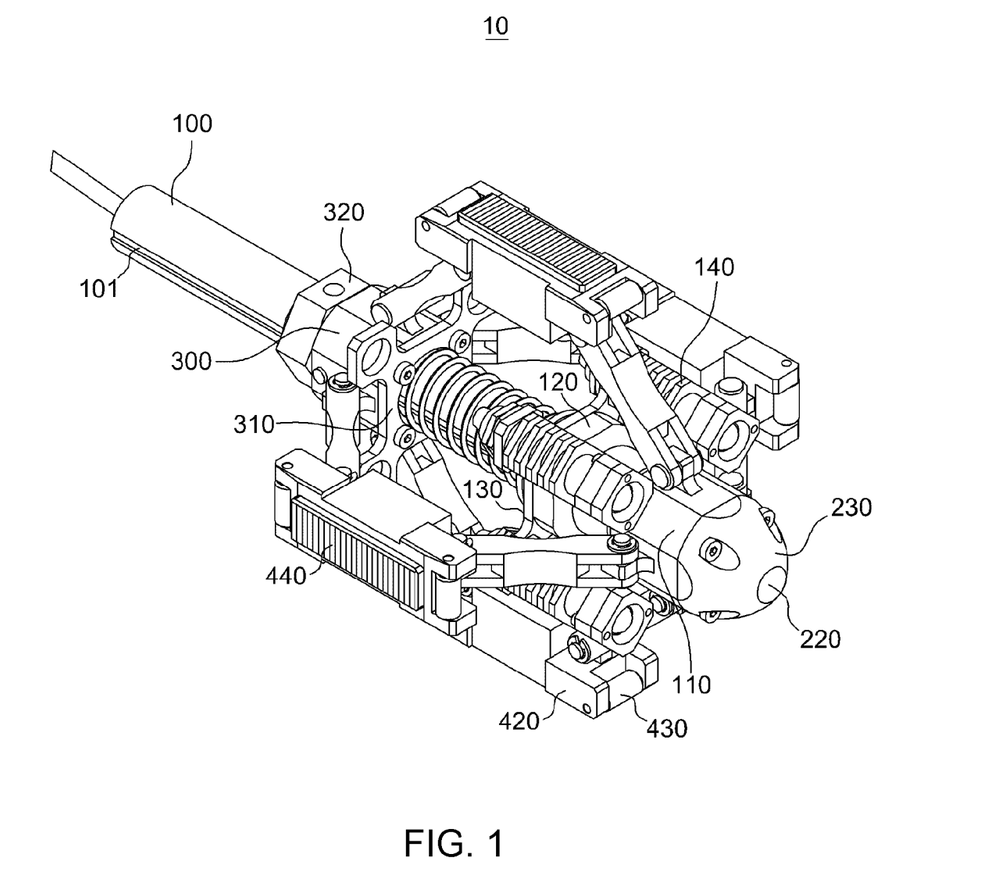
FIG. 1 is a perspective view of an inspecting device including link structures, according to an embodiment of the present invention.

FIG. 1 is a perspective view of an inspecting device 10 including link structures, according to an embodiment of the present invention.

The inspecting device 10 may include a frame 100 having a column shape extending in a longitudinal direction thereof and including a guide hole 101 formed in a side of the frame 100, a head unit 200 including a camera module installed at a fore-end of the frame 100, a first body unit 110 including a plurality of brackets 111 formed on an external surface thereof fixed to the frame 100 and screwed to the head unit 200, a support 120 formed on a rear surface of the first body unit 110, a first plate 130 screwed to the support 120 and including a plurality of holes 131 formed therein, a illumination module unit 140 inserted into the holes 131 of the first plate 130, a second body unit 300 including a plurality of brackets formed on an external surface thereof and surrounding the frame 100, guide pins 302 inserted into the external surface of the second body unit 300, a second plate 310 screwed to the second body unit 300, a coiled spring 340 inserted into the first body unit 110 and the second body unit 300, a fixation unit 320 including bolt holes 330 formed therein and coupled to the second body unit 300, and a link unit 400 linked to brackets 111 and 301 that are formed on external surfaces of the first body unit 110 and the second body unit 300, respectively, so as to be compatible with varying diameters of a subject.

FIGS. 2A through 2E are exploded diagrams for explaining elements of the inspecting device 10 of FIG. 1, according to an embodiment of the present invention.

Figure 2A:
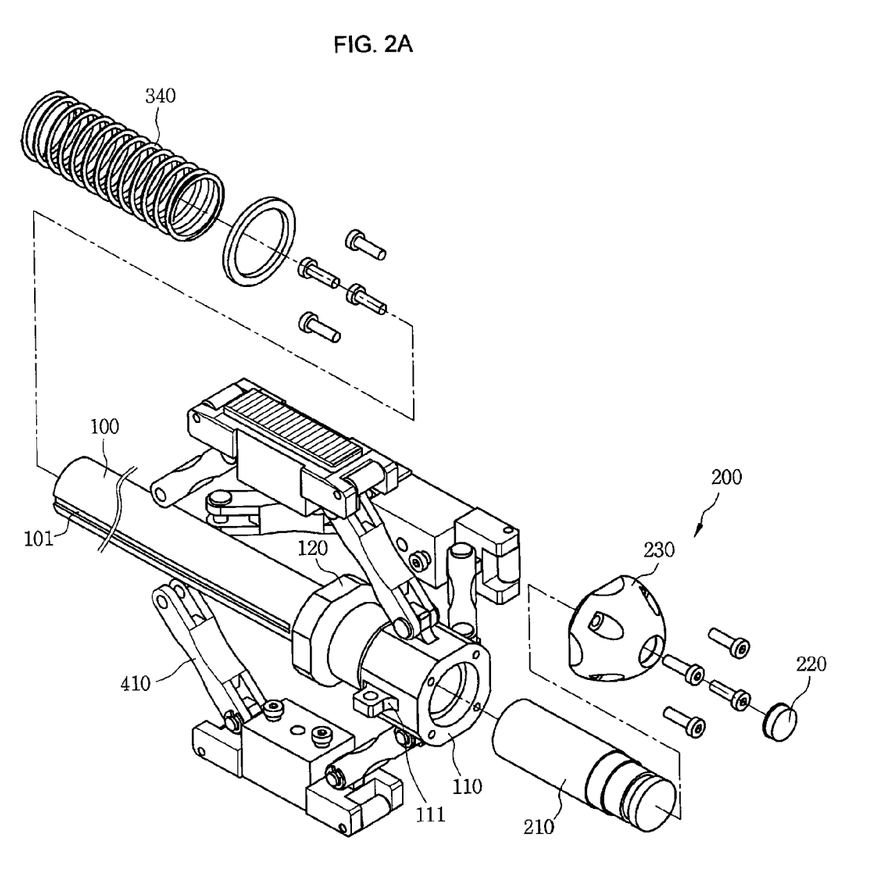
FIG. 2A is a perspective view of a frame and a fore-end portion of the frame, according to an embodiment of the present invention.

FIG. 2A is a perspective view of the frame 100 and a fore-end portion of the frame 100, according to an embodiment of the present invention.

The frame 100 has a column shape extending in a longitudinal direction thereof. In addition, the guide hole 101 may be formed in at least one side of the frame 100, and a connection cable is inserted into the frame 100.

The head unit 200 is installed at a fore-end of the frame 100, and includes the support 120 fixed to the frame 100, the first body unit 110 fixed on an upper end of the support 120, and a camera module inserted into the first body unit 110.

In detail, the support 120 supports the coiled spring 340 inserted into the inspecting device 10 so that the coiled spring 340 is compressed against the support 120.

The head unit 200 includes the camera module including a camera 210 and a lens 220, and a circular cap 230 for protecting the camera module. The camera 210 converts an image into an electric signal by using a charge-coupled device (CCD) and stores the electric signal in the form of digital data in a recording medium such as a flash memory.

The camera module is inserted into the first body unit 110, and first body unit 110 is screwed to the circular cap 230, thereby protecting the camera module. The brackets 111 are formed on the external surface of the first body unit 110 so the first body unit 110 may be coupled to the link structures.

Figure 2B:
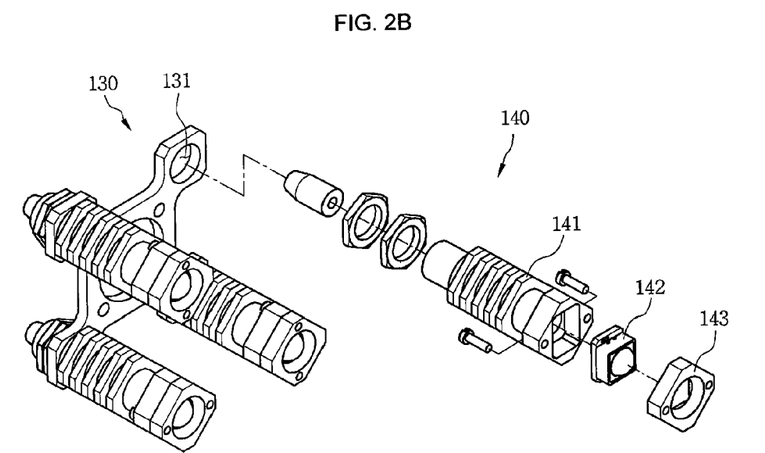
FIG. 2B is a perspective view of a illumination module unit of the inspecting device of FIG. 1, according to an embodiment of the present invention.

FIG. 2B is a perspective view of the illumination module unit 140 of the inspecting device 10 of FIG. 1, according to an embodiment of the present invention.

The first plate 130 surrounds the frame 100, and the holes 131 are integrally formed in an edge of the first plate 130. Referring to FIG. 1 and FIG. 2A, the first plate 130 is placed at the rear of the first body unit 110 and screwed to the support 120.

The illumination module unit 140 irradiates light into a tube of a subject in order to accurately inspect the subject, and is coupled into the holes 131 formed in the first plate 130.

That is, the first plate 130 is screwed to a rear surface of the support 120, and the illumination module unit 140 is inserted into and fixed to the holes 131 that are integrally formed in the first plate 130.

The illumination module unit 140 includes a housing 141, a light emitting diode (LED) light source 142 inserted into the housing 141, and a cover unit 143 for protecting the LED light source 142. In this case, at least one illumination module unit 140 may be provided, or alternatively four or more illumination module units 140 may be provided in order to uniformly irradiate light into the tube of the subject.

Figure 2C:
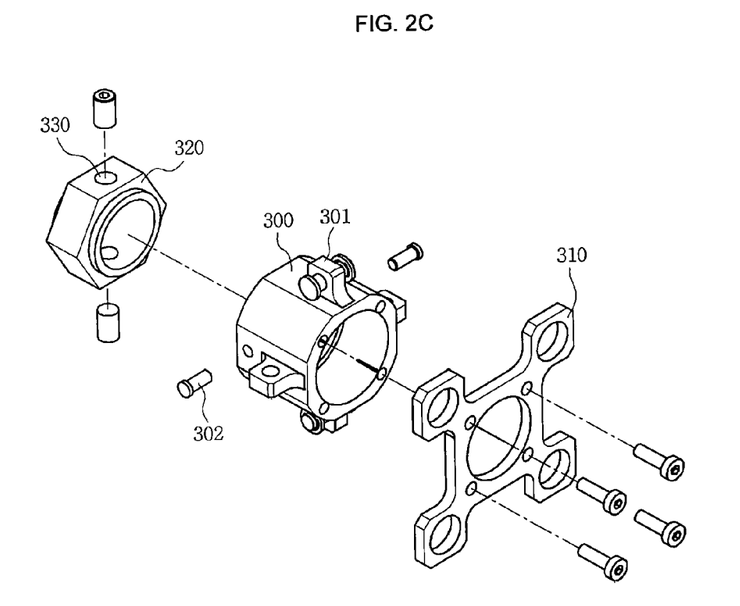
FIG. 2C is a perspective view of a rear-end portion of the inspecting device of FIG. 1, according to an embodiment of the present invention.

FIG. 2C is a perspective view of a rear-end portion of the inspecting device 10 of FIG. 1, according to an embodiment of the present invention.

Referring to FIG. 2C, the inspection device 10 includes the second plate 310, the second body unit 300 screwed to the second plate 310, and the fixation unit 320 mounted to the second body unit 300, wherein, the second body unit 300 surrounds the external surface of the frame 100.

The second plate 310 may have the same shape as that of the first plate 130, and may have any shape as long as the second plate 310 supports a spring coupled thereto.

The brackets 301 and the guide pins 302 are formed on the external surface of the second body unit 300. The guide pins 302 are formed so as to be movable along the guide holes 101 formed in the frame 100, and facilitates compression of the coiled spring 340. The rear end unit of the inspecting device 10 is fixed by moving the rear end unit of the inspecting device 10 along the guide hole 101 and then inserting a locking bolt into the bolt holes 330 formed in the fixation unit 320.

Figure 2D:
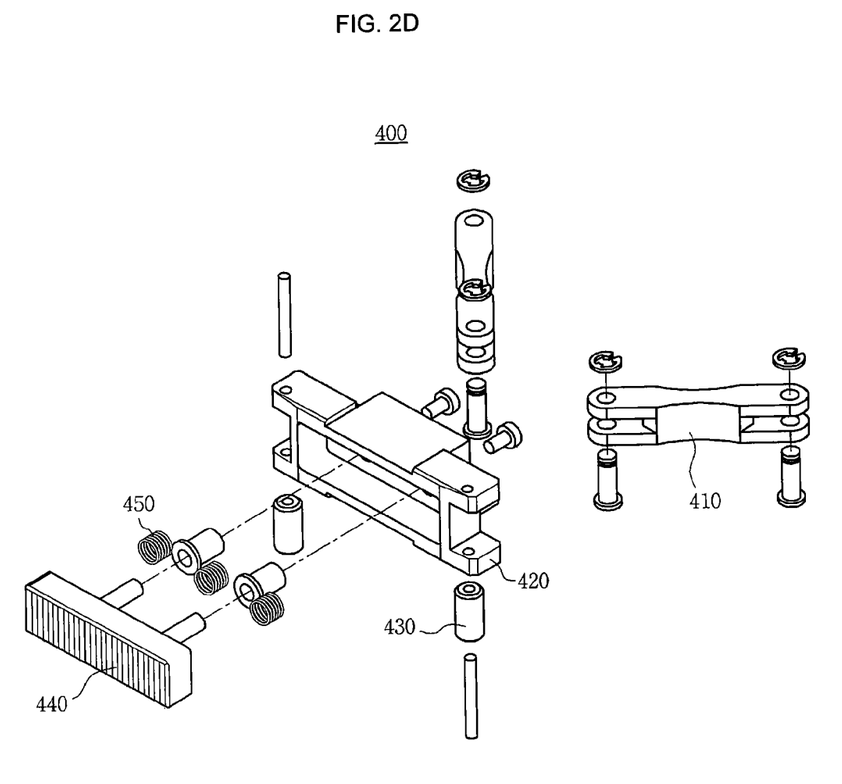
FIG. 2D is a perspective view of a link unit of the inspecting device of FIG. 1, according to an embodiment of the present invention.
Figure 2E:
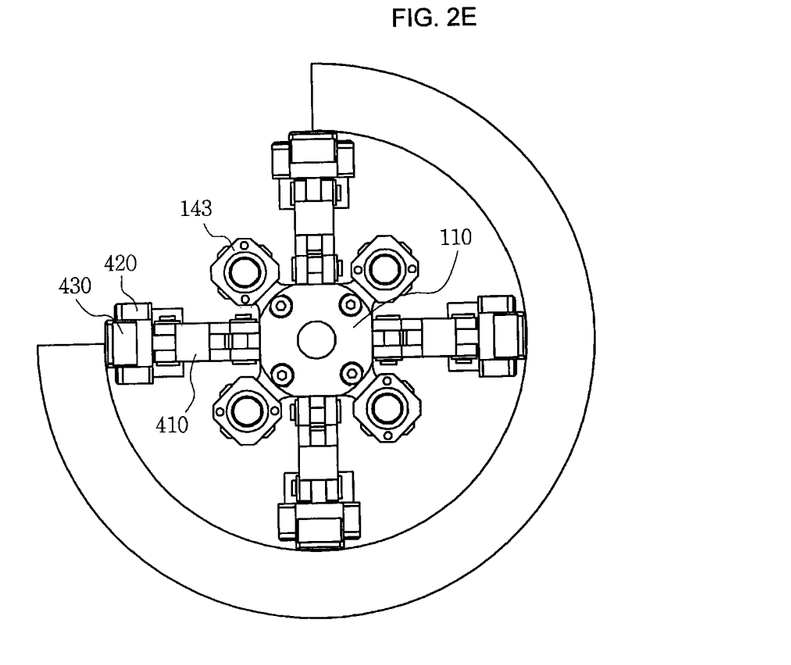
FIG. 2E is a side view of the inspecting device of FIG. 1.

FIG. 2D is a perspective view of the link unit 400 of the inspecting device 10 of FIG. 1, according to an embodiment of the present invention. FIG. 2E is a side view of the inspecting device 10 of FIG. 1, according to an embodiment of the present invention.

The link unit 400 includes the first body unit 110, levers 410 that are respectively coupled to the brackets 111 and 301 of the second body unit 300, a scanner housing 420 coupled to both axes of the lever 410, rollers 430 formed on both ends of the scanner housing 420, a scanner 440 fixed to an upper end of the scanner housing 420 and scanning a surface of the subject, and a plate spring 450 having a plate shape and formed under the scanner 440, which are disposed in the link unit 400.

The rollers 430 are formed on both ends of the housing 420. The rollers 430 reduces driving resistance of a driver of the inspecting device 10 when the inspecting device 10 proceeds forwards, and may have a crown shape so as to contact a wall of the subject in the form of a point or line.

The scanner 440 may be detachable from the scanner housing 420. A probe for a desired test is inserted into the scanner housing 420, and thus the scanner 440 may simultaneously perform phased array eddy current flaw detection and phased array ultrasonic flaw detection by using the probe.

As an example, the phased array ultrasonic wave testing may be performed by inserting a phased array ultrasonic wave oscillator having the form of an ultrasonic wave array, in which ultrasonic wave units are stacked in the scanner housing 420 in a width direction, into the scanner housing.

In this case, since the number of the link structures is four, four phased array ultrasonic wave oscillators may be inserted into the four link structures, or alternatively phased array ultrasonic wave oscillators may be inserted into one link structure or two link structure and a single sensor or a square sensor may be inserted into other remaining link structures.

The link unit 400 may further include a fixation unit (not shown) for inserting and fixing a sensor having various functions and an inspecting unit into the scanner housing 420.

FIG. 2E is a side view of the inspecting device 10 of FIG. 1, according to an embodiment of the present invention. Different four illumination module units 140 are diagonally formed on the first plate 130, and are coupled to brackets formed on the external surfaces of the first body unit 110 and the second body unit 300 so as to constitute the four link units 400.

Figure 3A:
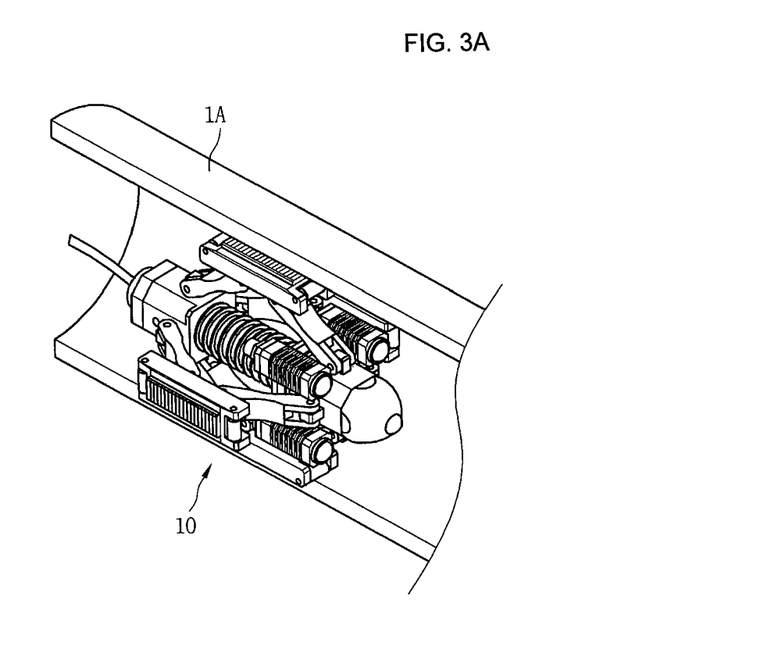
FIG. 3A is an inspecting conceptual diagram for explaining the case where the inspecting device inspects the inside of a narrow tube, according to an embodiment of the present invention.
Figure 3B:
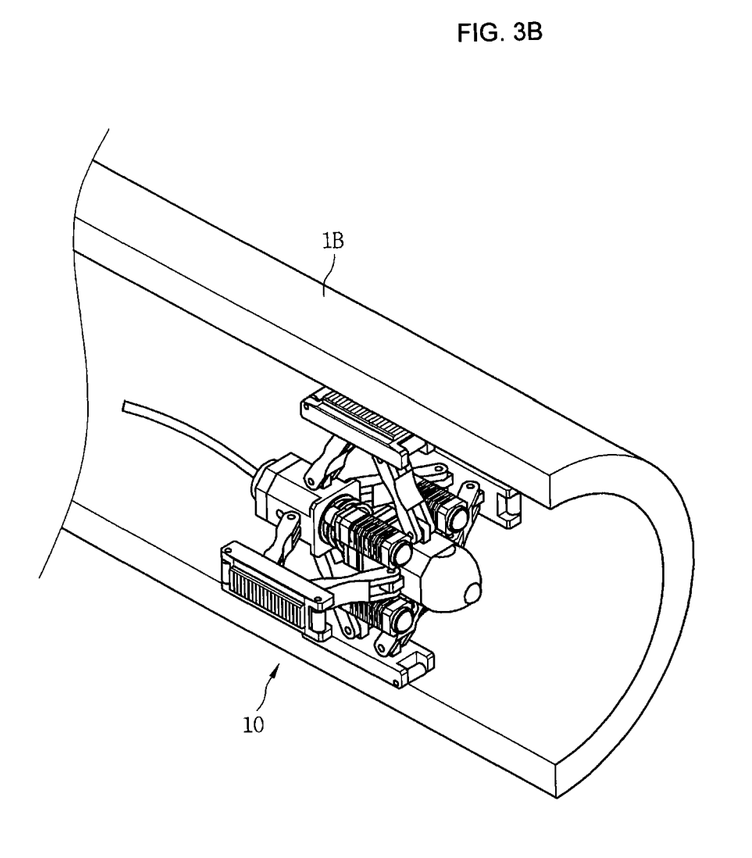
FIG. 3B is an inspecting conceptual diagram for explaining the case where the inspecting device inspects the inside of a wide tube, according to another embodiment of the present invention.

The operational relationship between the link unit 400 and the coiled spring 340 will be descried with reference to FIGS. 3A and 3B.

The coiled spring 340 is inserted into the first plate 130 and the second plate 310. That is, the coiled spring 340 is inserted into the inspecting device 10 so as to act an elastic force on the link unit 400, thereby covering relatively great displacement and compressing a wall of the link unit 400 at a predetermined force.

Thus, the coiled spring 340 and the plate spring 450 are doubly formed in the inspecting device 10. The plate spring 450 is disposed under the scanner 440 and inspects the wall. The coiled spring 340 is disposed at the center of the inspecting device 10 and covers relatively great displacement.

FIG. 3A is an inspecting conceptual diagram for explaining the case where the inspecting device 10 inspects an inside of a narrow tube 1A, according to an embodiment of the present invention. When the narrow tube 1A is inspected, the scanner 440 may inspect the wall of the narrow tube 1A while the scanner 440 of the link unit 400 is compressing the wall.

FIG. 3B is an inspecting conceptual diagram for explaining the case where the inspecting device 10 inspects the inside of a wide tube 1B, according to another embodiment of the present invention. While the coiled spring 340 is being compressed, the first body unit 110 and the second body unit 300 are compressed. In addition, the link unit 400 is widened and compresses the wall, and thus inspecting may be performed.

That is, in order to use the inspecting device 10 with respect to a circular space of a subject having various diameters, while the second body unit 300 is being moved along the guide holes 101 formed in both sides of the frame 100, the coiled spring 340 may be compressed and a locking bolt may be inserted into the bolt holes 330 formed in the fixation unit 320.

According to the above embodiments of the present invention, an inspecting device including various detachable probes may simultaneously perform visual testing and ultrasonic wave testing.

As described above, since the inspecting device includes a link structure, the inspecting device may inspect a subject having various diameters.

Moreover, since the inspecting device includes an illumination module unit, light may be irradiated to a dark inside of a tube so as to perform visual testing, thereby accurately performing inspection.

In addition, since the inspecting device provides correct information regarding a location, locations of defects existing on a subject may be accurately detected. Since various probes may be changeably used, ultrasonic wave testing and eddy current testing may be simultaneously performed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An inspecting device for inspecting a cylindrical subject and including a detachable probe, the inspecting device comprising:
    a frame having a column shape and extending in a longitudinal direction of the column, wherein a guide hole is formed in at least one side of the frame;
    a head unit comprising a camera module installed at a fore-end of the frame;
    a first body unit coupled to the head unit and comprising a plurality of brackets formed on an external surface of the first body unit;
    an illumination module unit installed into a hole formed in a plate wherein the plate is placed at the rear of the first body unit;
    a second body unit which surrounds the frame and comprises a plurality of brackets formed on an external surface of the second body unit;
    a coiled spring inserted into the first body unit and the second body unit; and
    a link unit coupled to the plurality of brackets formed on the external surface of the first body unit and the plurality of brackets formed on the external surface of the second body unit so as to be compatible with varying diameters of the cylindrical subject.

2. The inspecting device of claim 1, wherein the camera module of the head unit comprises:
    a camera and a lens that are inserted into the first body unit; and
    a circular cap for protecting the camera and the lens.

3. The inspecting device of claim 2, wherein the camera comprises a charge-coupled device (CCD) camera.

4. The inspecting device of claim 1, wherein a guide pine is inserted into the external surface of the second body unit.

5. The inspecting device of claim 1, wherein the illumination module unit comprises:
    a housing;
    a light emitting diode (LED) light source inserted into the housing; and
    a cover unit for protecting the LED light source.

6. The inspecting device of claim 1, wherein the link unit comprises:
    a pair of levers hinged to the plurality of brackets formed on the external surface of the first body unit and the plurality of brackets formed on the external surface of the second body unit;
    a scanner housing hinged to the pair of levers;
    rollers formed on both ends of the scanner housing;
    a scanner formed on an upper end of the scanner housing; and
    a plate spring formed under the scanner.

7. The inspecting device of claim 6, wherein the scanner comprises a detachable probe.

8. The inspecting device of claim 6, wherein each of the rollers has a crown shape so as to contact a wall of the cylindrical subject in the form of a line.

9. The inspecting device of claim 6, wherein the scanner has the form of an array in which a plurality of ultrasonic wave units are stacked in a width direction.

* * * * *